(12) United States Patent
Rizoiu et al.

(10) Patent No.: US 6,544,256 B1
(45) Date of Patent: Apr. 8, 2003

(54) ELECTROMAGNETICALLY INDUCED CUTTING WITH ATOMIZED FLUID PARTICLES FOR DERMATOLOGICAL APPLICATIONS

(75) Inventors: Ioana M. Rizoiu, Dana Point, CA (US); Andrew I. Kimmel, San Clemente, CA (US)

(73) Assignee: BioLase Technology, Inc., San Clemente, CA (US)

(*) Notice: Subject to any disclaimer, the term of this patent is extended or adjusted under 35 U.S.C. 154(b) by 0 days.

(21) Appl. No.: 09/298,112

(22) Filed: Apr. 23, 1999

Related U.S. Application Data
(60) Provisional application No. 60/083,003, filed on Apr. 24, 1998.

(51) Int. Cl.$^7$ .................................................. A61B 18/18
(52) U.S. Cl. .............................. 606/13; 606/3; 606/10; 606/167; 604/20; 604/291
(58) Field of Search .................... 606/3, 10–18, 606/167; 604/19–21, 27, 291

(56) References Cited

U.S. PATENT DOCUMENTS 5,411,502 A * 5/1995 Zair ............................. 606/10
5,741,247 A * 4/1998 Rizoiu et al. .................... 606/3
6,231,567 B1 * 5/2001 Rizoiu .......................... 606/10

OTHER PUBLICATIONS

Rizoiu et al "The Efficiency of Bone Ablation with an Nd: YAG Laser Beam Delivered with a Cooling Spray: An In Vitro Study"; Compend Contin, Educ. Dent; vol. XV, No. 1 1994 pp 106,108,110–112.*

"New Laser–Matter Interaction Concept to Enhance Hard Tissue Cutting Efficiency" by Rizoiu et al SPIE vol. 2134A (1994) Laser Tissue Interaction V pp 309–317.*

* cited by examiner

*Primary Examiner*—David M. Shay
(74) *Attorney, Agent, or Firm*—Stout, Uxa, Buyan & Mullins, LLP

(57) ABSTRACT

An electromagnetically induced mechanical cutting mechanism provides accurate cutting and ablating operations on soft tissues such as skin. Electromagnetic energy is concentrated into moist air and/or atomized fluid particles above the skin and, subsequently, the electromagnetic energy is absorbed by the moisture and/or atomized fluid particles to impart disruptive forces onto the skin. The moist air and/or atomized fluid particles may be medicated.

34 Claims, 7 Drawing Sheets

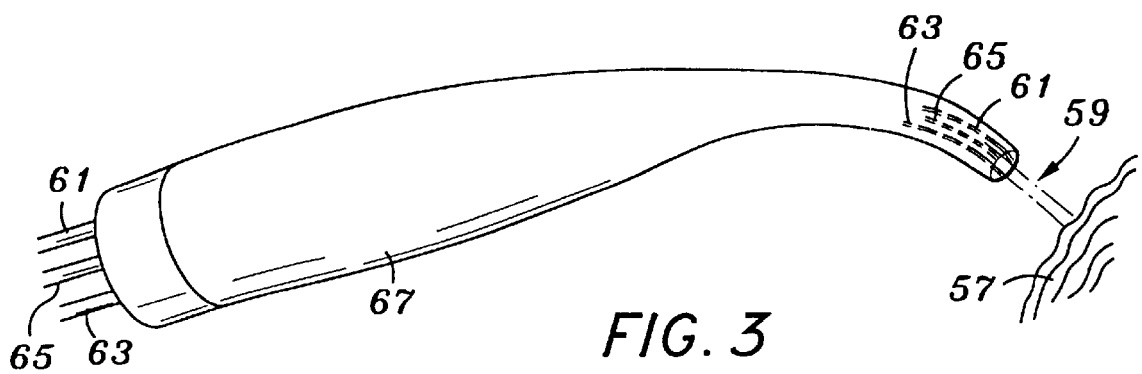
FIG. 3
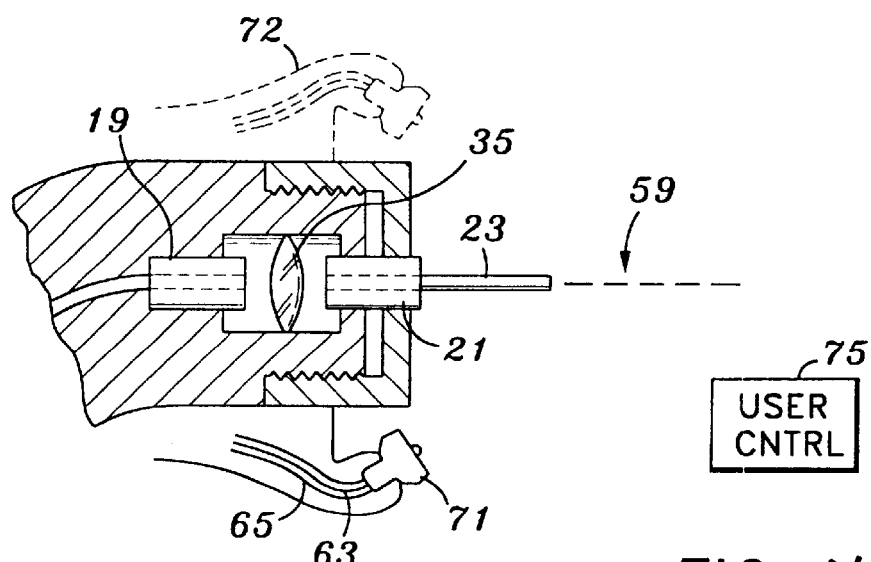
FIG. 4a
FIG. 4b
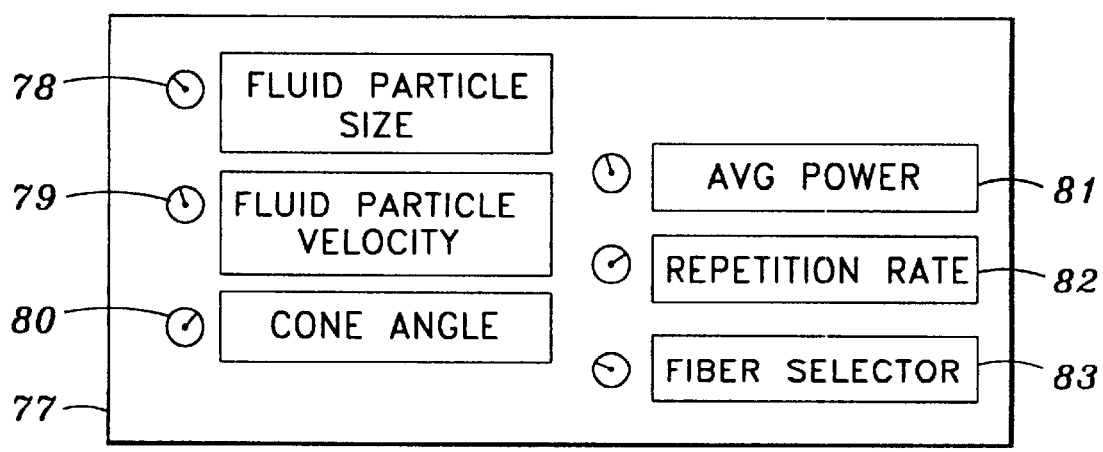
FIG. 5

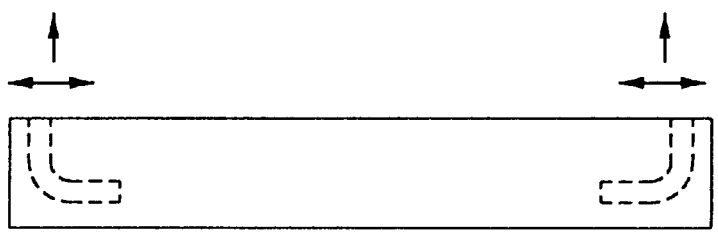 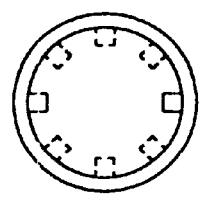
FIG. 6a  FIG. 6b
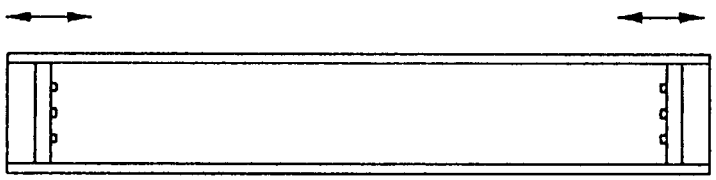 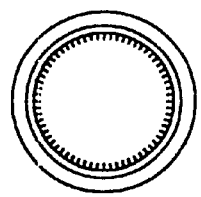
FIG. 7a  FIG. 7b
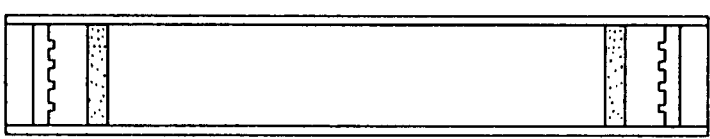 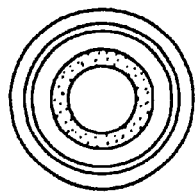
FIG. 8a  FIG. 8b

ELECTROMAGNETICALLY INDUCED CUTTING WITH ATOMIZED FLUID PARTICLES FOR DERMATOLOGICAL APPLICATIONS

PRIORITY INFORMATION

This application claims the benefit of U.S. Provisional Application No. 60/083,003 filed on Apr. 24, 1998 and entitled ELECTROMAGNETICALLY INDUCED CUTTING WITH ATOMIZED FLUID PARTICLES FOR DERMATOLOGICAL APPLICATIONS, the contents of which of which are expressly incorporated herein by reference.

BACKGROUND OF THE INVENTION

1. Field of the Invention

The present invention relates generally to medical apparatus and, more particularly, to methods and apparatus for cutting and removing tissue and other materials.

2. Description of Related Art

Turning to FIG. 1, a prior art optical cutter includes a fiber guide tube 5, a water line 7, an air line 9, and an air knife line 11 for supplying pressurized air. A cap 15 fits onto the hand-held apparatus 13 and is secured via threads 17. The fiber guide tube 5 abuts within a cylindrical metal piece 19. Another cylindrical metal piece 21 is a part of the cap 15. The pressurized air from the air knife line 11 surrounds and cools the laser as the laser bridges the gap between the two metal cylindrical objects 19 and 21. Air from the air knife line 11 flows out of the two exhausts 25 and 27 after cooling the interface between elements 19 and 21.

The Nd:YAG laser energy exits from the fiber guide tube 23 and is applied to a target surface of the patient. Water from the water line 7 and pressurized air from the air line 9 are forced into the mixing chamber 29. The air and water mixture is very turbulent in the mixing chamber 29, and exits this chamber through a mesh screen with small holes 31. The air and water mixture travels along the outside of the fiber guide tube 23, and then leaves the tube and contacts the area of surgery.

Other prior art devices include optical cutting systems utilizing the expansion of water to destroy and remove tooth material, such as disclosed in U.S. Pat. No. 5,199,870 to Steiner et al. This prior art approach requires a film of liquid having a thickness of between 10 and 200 μm. U.S. Pat. No. 5,267,856 to Wolbarsht et al. discloses a cutting apparatus that requires water to be inserted into pores of a material and then irradiated with laser energy. In both patents the precision and accuracy of the cut is highly dependent upon the precision and accuracy of the water film on the material or the water within the pores.

SUMMARY OF THE INVENTION

The present invention discloses an electromagnetically induced mechanical cutting mechanism, which can provide accurate cutting operations on hard and soft tissues, and other materials as well. Soft tissues may include fat, skin, mucosa, gingiva, muscle, heart, liver, kidney, brain, eye, and vessels, and hard tissue may include tooth enamel, tooth dentin, tooth cementum, tooth decay, amalgam, composites materials, tarter and calculus, bone and cartilage.

The electromagnetically induced cutter is capable of providing extremely fine and smooth incisions, irrespective of the cutting surface. Additionally, a user programmable combination of atomized particles or of a composition of moist air allows for user control of various cutting parameters. The various cutting parameters may also be controlled by changing spray nozzles and electromagnetic energy source parameters. The present invention further does not require any films of water or any particularly porous surfaces to obtain very accurate and controlled cutting. Since thermal heating is not used as the cutting mechanism in one embodiment, thermal damage can be attenuated or eliminated. Adjacent tissue can be spared from substantial thermal damage.

The electromagnetically induced mechanical cutter of the present invention includes an electromagnetic energy source, which focuses electromagnetic energy into a volume of air adjacent to a target surface. The target surface may comprise skin, for example. A user input device can specify a type of cut to be performed, and an atomizer (or moist air generating device) responsive to the user input device places moist air and/or a combination of atomized fluid particles into the volume of air. The electromagnetic energy is focused into the volume of air, and the wavelength of the electromagnetic energy is selected to be substantially absorbed by moisture in the air and/or the atomized fluid particles in the volume of air. Upon absorption of the electromagnetic energy the moisture and/or atomized fluid particles impart mechanical cutting forces onto the target surface.

The invention, together with additional features and advantages thereof may best be understood by reference to the following description taken in connection with the accompanying illustrative drawings.

BRIEF DESCRIPTION OF THE DRAWINGS

FIGS. 4a and 4b illustrate a preferred embodiment of the electromagnetically induced mechanical cutter;

FIGS. 1a–4aa and 5a–11a illustrate various configurations of the present invention for imparting electromagnetically-induced disruptive mechanical forces onto a target surface.

DESCRIPTION OF THE PRESENTLY PREFERRED EMBODIMENTS

Figure 2:
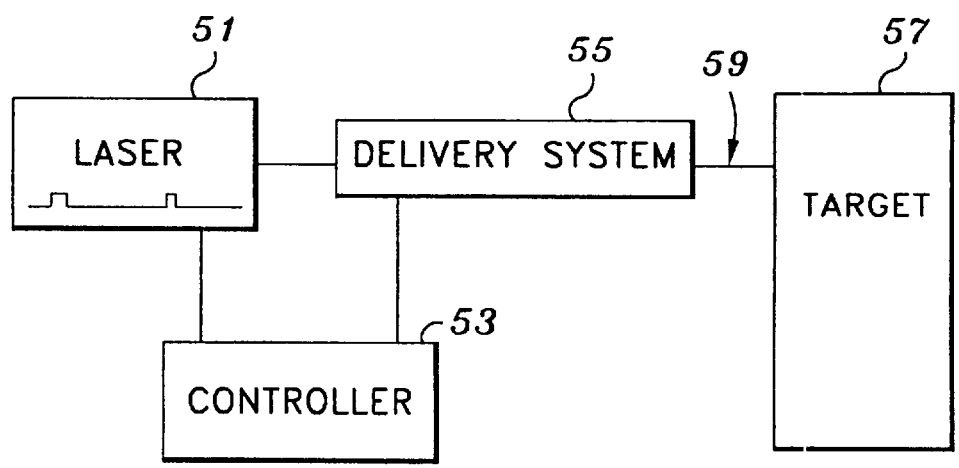
FIG. 2 is a schematic block diagram illustrating the electromagnetically induced mechanical cutter of the present invention.

FIG. 2 is a block diagram illustrating an electromagnetically induced mechanical cutter in accordance with the present invention. An electromagnetic energy source 51 is coupled to both a controller 53 and a delivery system 55. The delivery system 55 imparts mechanical forces onto the target surface 57. As presently embodied, the delivery system 55 comprises a fiber optic guide for routing the laser 51 into an interaction zone 59, located above the target surface 57. The delivery system 55 further comprises an atomizer for delivering user-specified combinations of atomized fluid particles into the interaction zone 59. The controller 53 controls various operating parameters of the laser 51, and further controls specific characteristics of the user-specified combination of atomized fluid particles output from the delivery system 55.

Figure 3A:
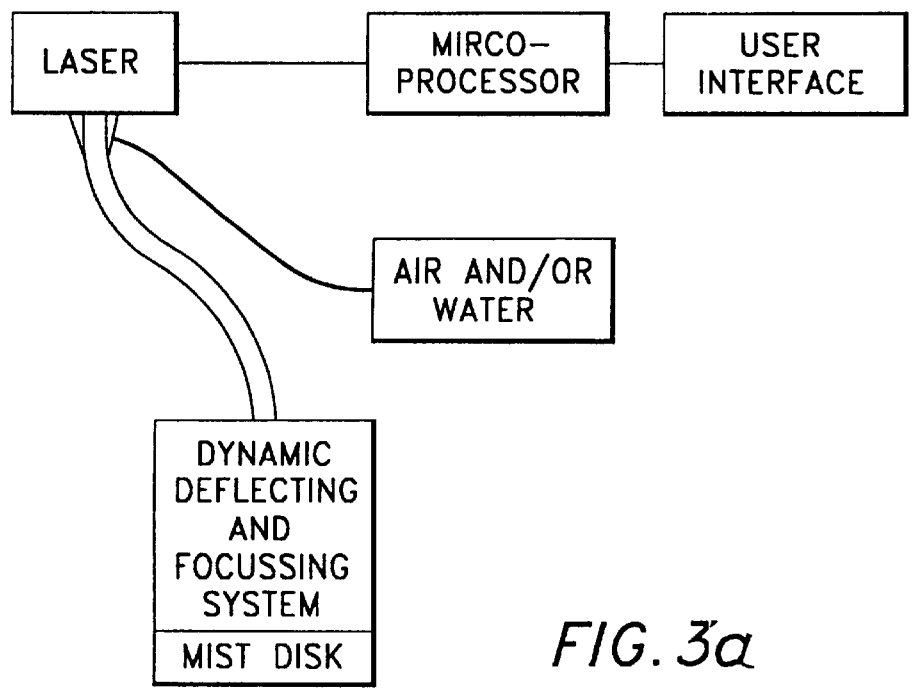
FIG. 3 illustrates one embodiment of the electromagnetically induced mechanical cutter of the present invention.

FIG. 3 shows a simple embodiment of the electromagnetically induced mechanical cutter of the present invention, in which a fiber optic guide 61, an air tube 63, and a water tube 65 are placed within a hand-held housing 67. The water tube 65 is operated under a relatively low pressure, and the air tube 63 is operated under a relatively high pressure. The laser energy from the fiber optic guide 61 focuses onto a combination of air and water, from the air tube 63 and the water tube 65, at the interaction zone 59. Atomized fluid particles in the air and water mixture absorb energy from the laser energy of the fiber optic tube 61, and explode. The explosive forces from these atomized fluid particles impart mechanical cutting forces onto the target surface 57.

Figure 1:
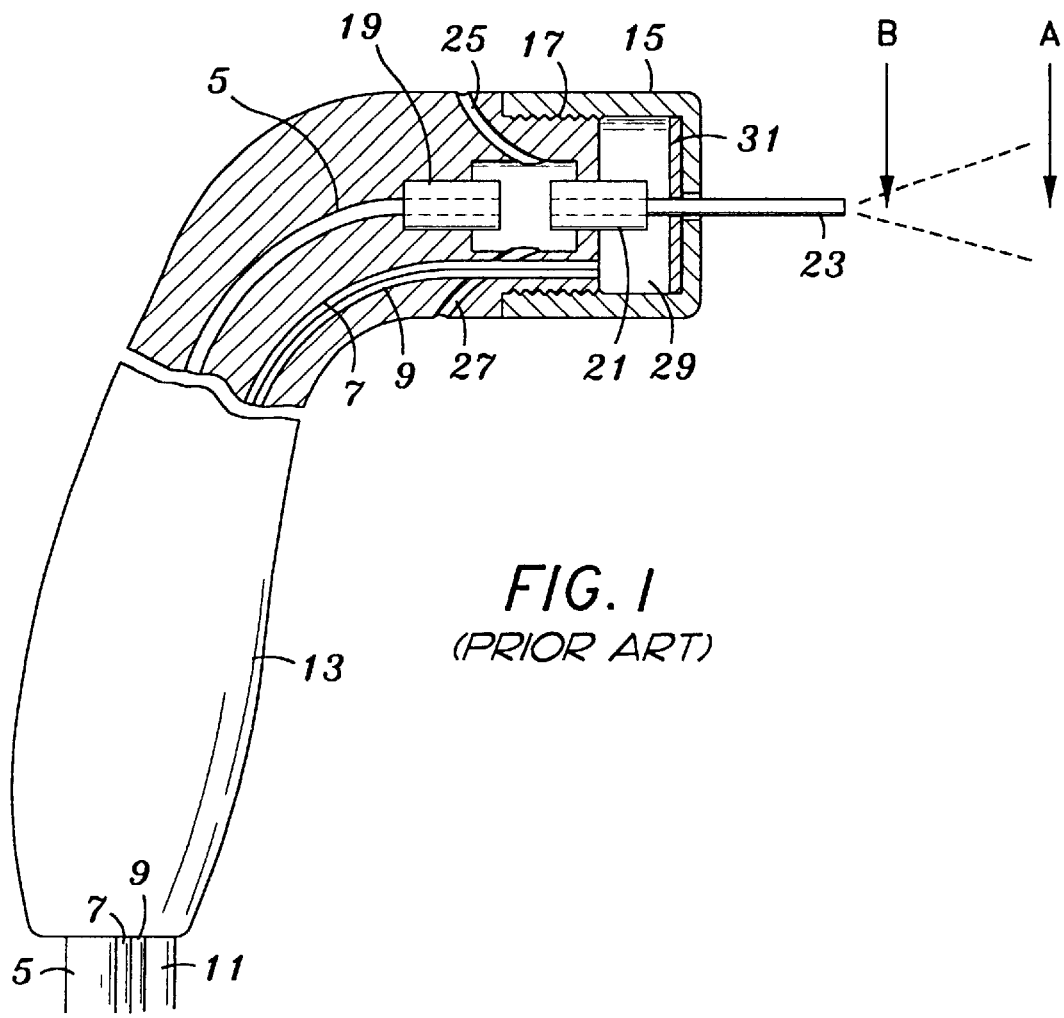
FIG. 1 is a conventional optical cutter apparatus.

Turning back to FIG. 1, the prior art optical cutter focuses laser energy onto a target surface at an area A, for example, and the electromagnetically induced mechanical cutter of the present invention focuses laser energy into an interaction zone B, for example. The prior art optical cutter uses the laser energy directly to cut tissue, and the electromagnetically induced mechanical cutter of the present invention uses the laser energy to expand atomized fluid particles to thus impart mechanical cutting forces onto the target surface. The prior art optical cutter must use a large amount of laser energy to cut the area of interest, and also must use a large amount of water to both cool this area of interest and remove cut tissue.

In contrast, the electromagnetically induced mechanical cutter of the present invention uses a relatively small amount of water and, further, uses only a small amount of laser energy to expand atomized fluid particles generated from the water. According to the electromagnetically induced mechanical cutter of the present invention, water is not needed to cool the area of surgery, since the exploded atomized fluid particles are cooled by exothermic reactions before they contact the target surface. Thus, atomized fluid particles of the present invention are heated, expanded, and cooled before contacting the target surface. The electromagnetically induced mechanical cutter of the present invention is thus capable of cutting without charring or discoloration.

Figure 4A:
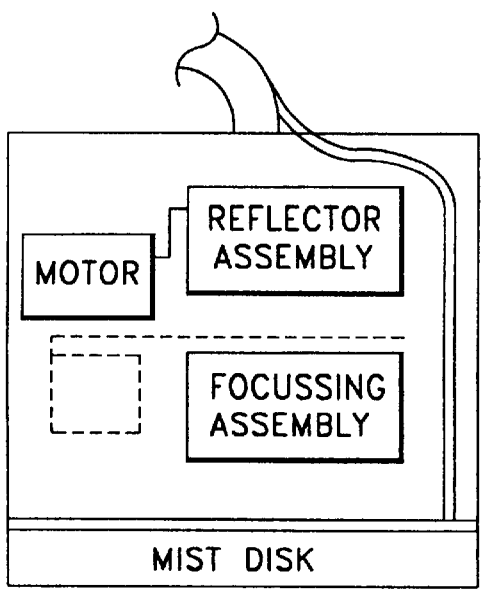

FIG. 4a illustrates the presently preferred embodiment of the electromagnetically induced mechanical cutter. The atomizer for generating atomized fluid particles comprises a nozzle 71, which may be interchanged with other nozzles (not shown) for obtaining various spatial distributions of the atomized fluid particles, according to the type of cut desired. A second nozzle 72, shown in phantom lines, may also be used. The cutting power of the electromagnetically induced mechanical cutter is further controlled by a user control 75 (FIG. 4b). In a simple embodiment, the user control 75 controls the air and water pressure entering into the nozzle 71. The nozzle 71 is thus capable of generating many different user-specified combinations of atomized fluid particles and aerosolized sprays.

Intense energy is emitted from the fiber optic guide 23. This intense energy is preferably generated from a coherent source, such as a laser. In the presently preferred embodiment, the laser comprises either an erbium, chromium, yttrium, scandium, gallium garnet (Er, Cr:YSGG) solid state laser, which generates electromagnetic energy having a wavelength in a range of 2.70 to 2.80 microns, or an erbium, yttrium, aluminum garnet (Er:YAG) solid state laser, which generates electromagnetic energy having a wavelength of 2.94 microns. As presently preferred, the Er, Cr:YSGG solid state laser has a wavelength of approximately 2.78 microns and the Er:YAG solid state laser has a wavelength of approximately 2.94 microns.

Although the fluid emitted from the nozzle 71 preferably comprises water, other fluids may be used and appropriate wavelengths of the electromagnetic energy source may be selected to allow for high absorption by the fluid. Other possible laser systems include an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YALO3) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide ($CO_2$), which generates electromagnetic energy having a wavelength in a range of 9.0 to 10.6 microns. Water is chosen as the preferred fluid because of its biocompatibility, abundance, and low cost. The actual fluid used may vary as long as it is properly matched (meaning it is highly absorbed) to the selected electromagnetic energy source (i.e. laser) wavelength.

The electromagnetic energy source can be configured with the repetition rate greater than 1 Hz, the pulse duration range between 1 picosecond and 1000 microseconds, and the energy greater than 1 milliJoule per pulse. According to one operating mode of the present invention, the electromagnetic energy source has a wavelength of approximately 2.78 microns, a repetition rate of 20 Hz, a pulse duration of 140 microseconds, and an energy between 1 and 300 milliJoules per pulse.

In one preferred embodiment the electromagnetic energy source has a pulse duration on the order of nanoseconds, which is obtained by Q-switching the electromagnetic energy source, and in another preferred embodiment the electromagnetic energy source has a pulse duration on the order of picoseconds, which is obtained by mode locking the electromagnetic energy source. Q-switching is a conventional mode of laser operation which is extensively employed for the generation of high pulse power. The textbook, Solid-State Laser Engineering, Fourth Extensively Revised and Updated Edition, by Walter Koechner and published in 1996, the entire contents of which are expressly incorporated herein by reference, discloses Q-switching laser theory and various Q-switching devices. Q-switching devices generally inhibit laser action during the pump cycle by either blocking the light path, causing a mirror misalignment, or reducing the reflectivity of one of the resonator mirrors. Near the end of the flashlamp pulse, when maximum energy has been stored in the laser rod, a high Q-condition is established and a giant pulse is emitted from the laser. Very fast electronically controlled optical shutters can be made by using the electro-optic effect in crystals or liquids. An acousto-optic Q-switch launches an ultrasonic wave into a block of transparent optical material, usually fused silica. Chapter eight of the textbook, Solid-State Laser Engineering, Fourth Extensively Revised and Updated Edition, discloses the above-mentioned and other various Q-switching devices. Mode locking is a conventional procedure which phase-locks the longitudinal modes of the laser and which uses a pulse width that is inversely related to the bandwidth of the laser emission. Mode locking is discussed on pages 500–561 of the above-mentioned textbook entitled, Solid-State Laser Engineering, Fourth Extensively Revised and Updated Edition.

The atomized fluid particles provide the mechanical cutting forces when they absorb the electromagnetic energy within the interaction zone. These atomized fluid particles, however, provide a second function of cleaning and cooling the fiber optic guide from which the electromagnetic energy is output. The delivery system 55 (FIG. 2) for delivering the electromagnetic energy includes a fiber optic energy guide or equivalent which attaches to the laser system and travels to the desired work site. Fiber optics or waveguides are typically long, thin and lightweight, and are easily manipulated. Fiber optics can be made of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, germanium oxide (GeO2), and other materials. Other delivery systems include devices comprising mirrors, lenses and other optical components where the energy travels through a cavity, is directed by various mirrors, and is focused onto the targeted cutting site with specific lenses. The preferred embodiment of light delivery for medical applications of the present invention is through a fiber optic conductor, because of its light weight, lower cost, and ability to be packaged inside of a handpiece of familiar size and weight to the surgeon, dentist, or clinician. In industrial and other applications, non-fiber optic systems may be used.

The nozzle 71 is employed to create an engineered combination of small particles of the chosen fluid. The nozzle 71 may comprise several different designs including liquid only, air blast, air assist, swirl, solid cone, etc. When fluid exits the nozzle 71 at a given pressure and rate, it is transformed into particles of user-controllable sizes, velocities, and spatial distributions. The nozzle may have spherical, oval, or other shaped openings of any of a variety of different sizes, according to design parameters.

Figure 5A:
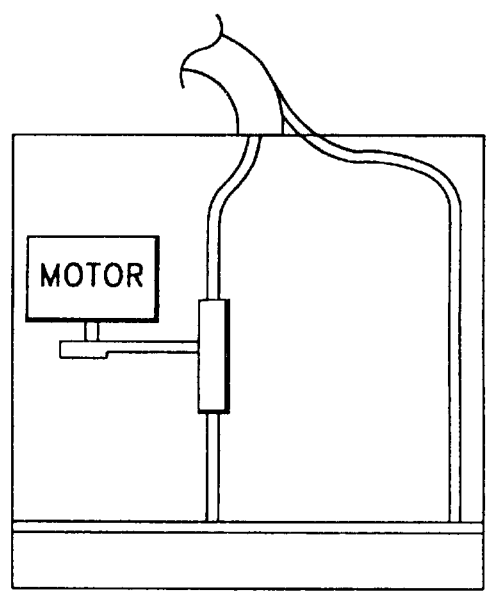
FIG. 5 illustrates a control panel for programming the combination of atomized fluid particles according to the present invention.

FIG. 5 illustrates a control panel 77 for allowing user-programmability of the atomized fluid particles. By changing the pressure and flow rates of the fluid, for example, the user can control the atomized fluid particle characteristics. These characteristics determine absorption efficiency of the laser energy, and the subsequent cutting effectiveness of the electromagnetically induced mechanical cutter. This control panel may comprise, for example, a fluid particle size control 78, a fluid particle velocity control 79, a cone angle control 80, an average power control 81, a repetition rate 82 and a fiber selector 83.

The cone angle may be controlled, for example, by changing the physical structure of the nozzle 71. Various nozzles 71 may be interchangeably placed on the electromagnetically induced mechanical cutter. Alternatively, the physical structure of a single nozzle 71 may be changed.

Figure 6:
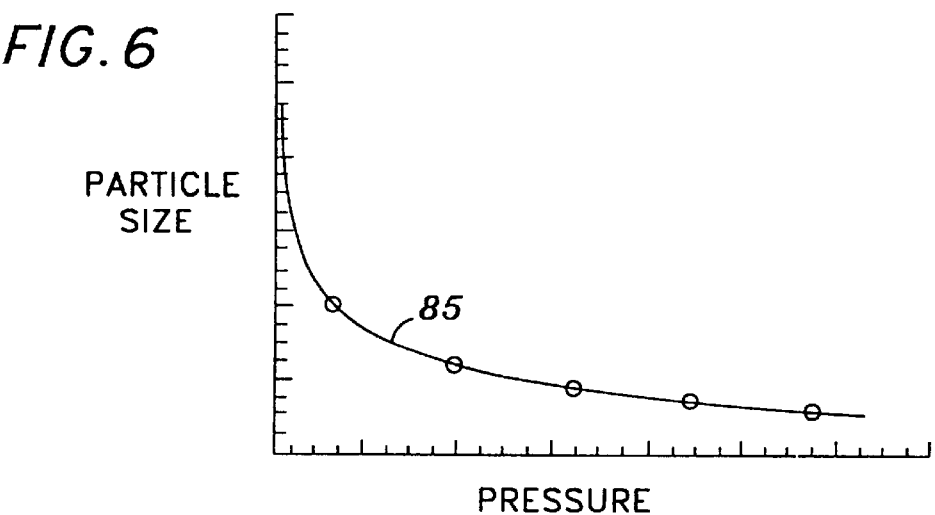
FIG. 6 is a plot of particle size versus fluid pressure.
Figure 7:
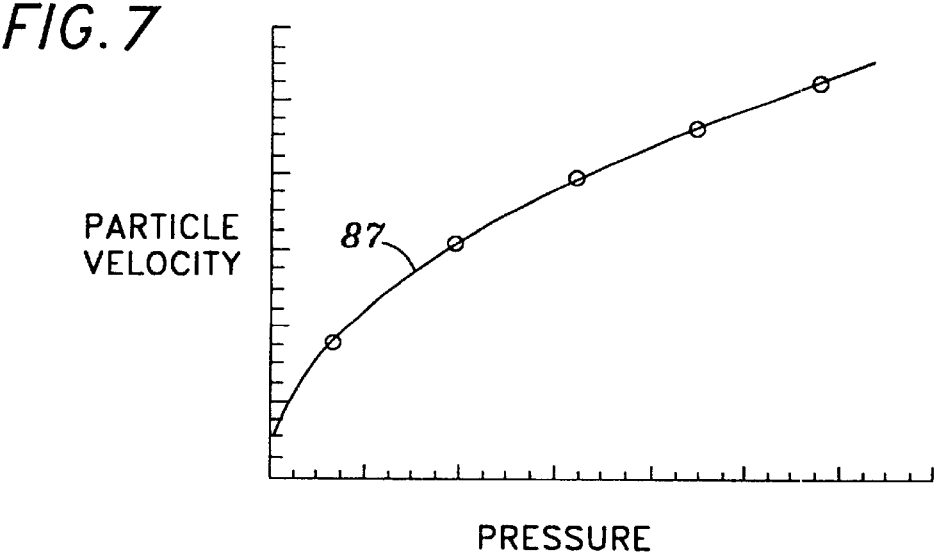
FIG. 7 is a plot of particle velocity versus fluid pressure.

FIG. 6 illustrates a plot 85 of mean fluid particle size versus pressure. According to this figure, when the pressure through the nozzle 71 is increased, the mean fluid particle size of the atomized fluid particles decreases. The plot 87 of FIG. 7 shows that the mean fluid particle velocity of these atomized fluid particles increases with increasing pressure.

According to the present invention, materials can be removed in one embodiment from a target surface by mechanical cutting forces, instead of by conventional thermal cutting forces. In another embodiment, the apparatus of the present invention can be used to impart thermal energy onto the tissue subsequent to the non-thermal cutting or ablating, for inducing coagulation, for example. For example, a first scan can induce non-thermal or reduced thermal cutting, and a subsequent scan can be used to apply thermal energy to the surface for inducing coagulation. In yet another embodiment, a reduced amount of atomized fluid particles (or moisture) may be used to simultaneously impart a combination of mechanical cutting (from expanding moisture) and thermal cutting (from the laser to impart coagulation, for example). Laser energy is used only to induce mechanical forces onto the targeted material. Thus, the atomized fluid particles act as the medium for transforming the electromagnetic energy of the laser into the mechanical energy required to achieve the mechanical cutting effect of the present invention. The laser energy itself is not directly absorbed by the targeted material. The mechanical interaction of the present invention is safer, faster, and can at least partially eliminate negative thermal side-effects typically associated with conventional laser cutting systems.

The fiber optic guide 23 (FIG. 4a) can be placed into close proximity of the target surface. This fiber optic guide 23, however, does not actually contact the target surface. Since the atomized fluid particles from the nozzle 71 are placed into the interaction zone 59, the purpose of the fiber optic guide 23 is for placing laser energy into this interaction zone, as well. One feature of the present invention is the formation of the fiber optic guide 23 of straight or bent sapphire. Regardless of the composition of the fiber optic guide 23, however, another feature of the present invention is the cleaning effect of the air and water, from the nozzle 71, on the fiber optic guide 23.

The present inventors have found that this cleaning effect is optimal when the nozzle 71 is pointed somewhat directly at the target surface. For example, debris from the mechanical cutting are removed by the spray from the nozzle 71.

Figure 8:
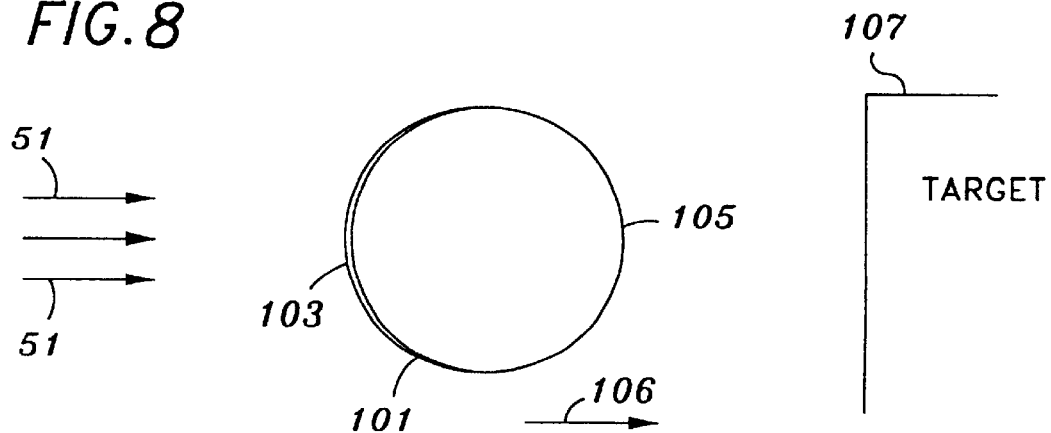
FIG. 8 is a schematic diagram illustrating a fluid particle, a source of electromagnetic energy, and a target surface according to the present invention.

Additionally, the present inventors have found that this orientation of the nozzle 71, pointed toward the target surface, enhances the cutting efficiency of the present invention. Each atomized fluid particle contains a small amount of initial kinetic energy in the direction of the target surface. When electromagnetic energy from the fiber optic guide 23 contacts an atomized fluid particle, the exterior surface of the fluid particle acts as a focusing lens to focus the energy into the water particle's interior. As shown in FIG. 8, the water particle 101 has an illuminated side 103, a shaded side 105, and a particle velocity 107. The focused electromagnetic energy is absorbed by the water particle 101, causing the interior of the water particle to heat and explode rapidly. This exothermic explosion cools the remaining portions of the exploded water particle 101. The surrounding atomized fluid particles further enhance cooling of the portions of the exploded water particle 101. A pressure-wave is generated from this explosion. This pressure-wave, and the portions of the exploded water particle 101 of increased kinetic energy, are directed toward the target surface 107. The incident portions from the original exploded water particle 101, which are now traveling at high velocities with high kinetic energies, and the pressure-wave, impart strong, concentrated, mechanical forces onto the target surface 107.

These mechanical forces cause the target surface 107 to break apart from the material surface through a "chipping away" action. The target surface 107 does not undergo vaporization, disintegration, or charring. The chipping away process can be repeated by the present invention until the desired amount of material has been removed from the target surface 107. Unlike prior art systems, the present invention does not require a thin layer of fluid. In fact, it is preferred that a thin layer of fluid does not cover the target surface, since this insulation layer would interfere with the above-described interaction process.

The nozzle 71 is preferably configured to produce atomized sprays with a range of fluid particle sizes narrowly distributed about a mean value. The user input device for controlling cutting efficiency may comprise a simple pressure and flow rate gauge 75 (FIG. 4b) or may comprise a control panel as shown in FIG. 5, for example. Upon a user input for a high resolution cut, relatively small fluid particles are generated by the nozzle 71. Relatively large fluid particles are generated for a user input specifying a low resolution cut. A user input specifying a deep penetration cut causes the nozzle 71 to generate a relatively low density distribution of fluid particles, and a user input specifying a shallow penetration cut causes the nozzle 71 to generate a relatively high density distribution of fluid particles. If the user input device comprises the simple pressure and flow rate gauge 75 of FIG. 4b, then a relatively low density distribution of relatively small fluid particles can be generated in response to a user input specifying a high cutting efficiency. Similarly, a relatively high density distribution of relatively large fluid particles can be generated in response to a user input specifying a low cutting efficiency.

Soft tissues may include fat, skin, mucosa, gingiva, muscle, heart, liver, kidney, brain, eye, and vessels, and hard tissue may include tooth enamel, tooth dentin, tooth cementum, tooth decay, amalgam, composites materials, tarter and calculus, bone, and cartilage. The term "fat" refers to animal tissue consisting of cells distended with greasy or oily matter. Other soft tissues such as breast tissue, lymphangiomas, and hemangiomas are also contemplated. The hard and soft tissues may comprise human tissue or other animal tissue. Other materials may include glass and semiconductor chip surfaces, for example. The electromagnetically induced mechanical cutting mechanism can be further be used to cut or ablate other biological materials, ceramics, cements, polymers, porcelain, and implantable materials and devices including metals, ceramics, and polymers. The electromagnetically induced cutting mechanism can also be used to cut or ablate surfaces of metals, plastics, polymers, rubber, glass and crystalline materials, concrete, wood, cloth, paper, leather, plants, and other man-made and naturally occurring materials. Biological materials can include plaque, tartar, a biological layer or film of organic consistency, a smear layer, a polysaccharide layer, and a plaque layer. A smear layer may comprise fragmented biological material, including proteins, and may include living or decayed items, or combinations thereof. A polysaccharide layer will often comprise a colloidal suspension of food residue and saliva. Plaque refers to a film including food and saliva, which often traps and harbors bacteria therein. These layers or films may be disposed on teeth, other biological surfaces, and nonbiological surfaces. Metals can include, for example, aluminum, copper, and iron.

The set various parameters can be adjusted according to the type of cut and the type of target surface. In the case of bone tissues, for example, a portion of cancer affected bone may be removed by the electromagnetically induced mechanical cutter of the present invention. The electromagnetically induced mechanical cutter of the present invention provides a clean, high-precision cut with minimized cross-contamination, and thus allows for a precise removal of the cancer affected bone. After the bone is cut, it tends to grow back with an increased success rate and with a reduction in the likelihood of cross-contamination.

A user may adjust the combination of atomized fluid particles exiting the nozzle 71 to efficiently implement cooling and cleaning of the fiber optic guide 23 (FIG. 4a), as well. According to the present invention, the combination of atomized fluid particles may comprise a distribution, velocity, and mean diameter to effectively cool the fiber optic guide 23, while simultaneously keeping the fiber optic guide 23 clean of particular debris which may be introduced thereon by the surgical site.

Looking again at FIG. 8, electromagnetic energy contacts each atomized fluid particle 101 on its illuminated side 103 and penetrates the atomized fluid particle to a certain depth. The focused electromagnetic energy is absorbed by the fluid, inducing explosive vaporization of the atomized fluid particle 101.

The diameters of the atomized fluid particles can be less than, almost equal to, or greater than the wavelength of the incident electromagnetic energy. In each of these three cases, a different interaction occurs between the electromagnetic energy and the atomized fluid particle. When the atomized fluid particle diameter is less than the wavelength of the electromagnetic energy ($d<\lambda$), the complete volume of fluid inside of the fluid particle 101 absorbs the laser energy, inducing explosive vaporization. The fluid particle 101 explodes, ejecting its contents radially. As a result of this interaction, radial pressure-waves from the explosion are created and projected in the direction of propagation. The resulting portions from the explosion of the water particle 101, and the pressure-wave, produce the "chipping away" effect of cutting and removing of materials from the target surface 107. When the fluid particle 101 has a diameter, which is approximately equal to the wavelength of the electromagnetic energy ($d\approx\lambda$) the laser energy travels through the fluid particle 101 before becoming absorbed by the fluid therein. Once absorbed, the distal side (laser energy exit side) of the fluid particle heats up, and explosive vaporization occurs. In this case, internal particle fluid is violently ejected through the fluid particle's distal side, and moves rapidly with the explosive pressure-wave toward the target surface. The laser energy is able to penetrate the fluid particle 101 and to be absorbed within a depth close to the size of the particle's diameter. When the diameter of the fluid particle is larger than the wavelength of the electromagnetic energy ($d>\lambda$), the laser energy penetrates the fluid particle 101 only a small distance through the illuminated surface 103 and causes this illuminated surface 103 to vaporize. The vaporization of the illuminated surface 103 tends to propel the remaining portion of the fluid particle 101 toward the targeted material surface 107. Thus, a portion of the mass of the initial fluid particle 101 is converted into kinetic energy, to thereby propel the remaining portion of the fluid particle 101 toward the target surface with a high kinetic energy. This high kinetic energy is additive to the initial kinetic energy of the fluid particle 101. The effects can be visualized as a micro-hydro rocket with a jet tail, which helps propel the particle with high velocity toward the target surface 107. The electromagnetically induced mechanical cutter of the present invention can generate a high resolution cut. Unlike the cut of the prior art, the cut of the present invention is clean and precise. Among other advantages, this cut provides an ideal bonding surface, is accurate, and does not stress remaining materials surrounding the cut.

FIGS. 1a–11a illustrate various configurations of the present invention for imparting non-thermal electromagnetically-induced disruptive mechanical forces, and/or thermal cutting forces, onto a target surface, such as skin.

A primary purpose of the present invention is to place electromagnetic energy, from an Er:YSGG laser, for example, into an atomized distribution of fluid particles, above the target surface. The energy from the laser is absorbed by the atomized fluid particles, causing the atomized fluid particles to expand and impart disruptive mechanical forces onto the target surface. A key feature of the present invention is the absorption of the electromagnetic radiation by the fluid particles in the interaction zone, and the subsequent mechanical cutting imparted to the target surface. The term "cutting" is intended to encompass ablating and other types of disruptive mechanical forces that can be imparted onto a target surface.

Applicants have found that the distribution of particles imparted onto or directly in front of a fiber optic tip can form an interaction zone in front of the tip. The fiber optic serves to transport the concentrated electromagnetic energy through extraneous or stray fluid particles and into what Applicants refer to as an interaction zone, where high absorption of the electromagnetic energy subsequently occurs near to the target. Applicants have observed that the presently embodied electromagnetic radiation, which is highly absorbed by the specified fluid, and the combining of this electromagnetic radiation with the fluid particles at the tip of a fiber optic, will limit the penetration of the electromagnetic radiation through the mist to a predetermined depth. After this depth any electromagnetic radiation continuing through the mist is undetectable or negligible, relative to the particular application at hand. As the electromagnetic radiation passes further and further into the interaction zone, its energy is absorbed more and more by the fluid particles, until hardly any, and eventually none, of the electromagnetic radiation remains. There is a point, or zone, wherein the thermal cutting forces are reduced substantially or eliminated, and wherein the cutting forces from the absorption of the electromagnetic radiation by the fluid particles, is optimal.

The high absorption of the electromagnetic energy by the fluid particles, resulting in expansion of the fluid particles, is a key element of the present invention. A target must be placed within or near this interaction zone in order for the disruptive mechanical forces, from the absorption of the electromagnetic radiation by the fluid particles, to be optimally imparted onto the target surface.

One feature of the present invention is to maintain a bounded layer of fluid particles, which is not too thick and which is not too thin. The bounded layer of fluid particles must be of a relatively high density in order to optimize the absorption of electromagnetic energy in the layer and to ensure that substantial thermal cutting forces from the electromagnetic energy are attenuated and preferably substantially eliminated, being transformed into the fluid particles instead, so that the expansion of the fluid particles performs the cutting of the target surface. A relatively low-density distribution of fluid particles, spanning a relatively large distance, would absorb the incident electromagnetic radiation, resulting in fluid particles expanding well above the target surface. Any remaining radiation in the fluid particle distribution near the target surface would be too weak to induce the required high absorption and resulting mechanical cutting forces.

In addition to being bounded to enable the delivery of concentrated electromagnetic energy into the layer of fluid particles, the layer must be bounded to facilitate the very-close positioning of the target surface to the incident electromagnetic radiation. More particularly, the target surface must be placed at the boundary or within the interaction zone, so that the disruptive mechanical forces resulting from the expansion of the fluid particles occur near the target and do not need to travel far before being imparted onto the target. Thus, it can be seen that a fiber optic tip placed into a distribution of fluid particles and, additionally, placed in close proximity (2–3 mm, for example) of a target surface, creates a thin layer of fluid particles between the incident, concentrated electromagnetic energy and the target surface. Other distances are possible within the scope of the present invention, depending on, for example, the selected laser intensity and wavelength, the selected fluid, and the selected distribution of atomized fluid particles. The below embodiments explore other means for creating a bounded layer of fluid particles between the incident, concentrated electromagnetic energy and the target surface.

Turning to FIG. 1*a*, an electromagnetically induced mechanical cutter is illustrated comprising a laser, microprocessor and user interface. The electromagnetically induced mechanical cutter further comprises an air and/or water source for supplying one or more atomization nozzles with air and/or water. A scanning housing is connected between the motor and the air and/or water supply. The scanning housing inputs optical energy from the laser, and further inputs air and/or water from the air and/or water supply. Both the motor and the laser are preferably controlled by the microprocessor in accordance with one or more user inputs from the user interface. The motor is adapted to scan both the fiber optic from the laser and at least one atomization nozzle connected to the air and/or water supply, to achieve predetermined scanning patterns on the surface of the target.

In the illustrated embodiment, the scanning housing is placed directly onto or supported above the target, such as the patient's skin, and the motor moves both the fiber optic and the attached atomization nozzles, to achieve predetermined scanning patterns on the target. In the illustrated embodiment, the two atomization nozzles are fixed to a fiber optic coupler by arms, and the air and water lines connected to the atomization nozzles are flexible. Additionally, in one preferred embodiment, the fiber optic from the laser within the scanning housing is flexible to allow deflection by the motor. U.S. Pat. Nos. 5,474,549 and 5,336,217 disclose fibers that are deflected to achieve scanning patterns on a target surface. The entire contents of these two patents are incorporated herein by reference to illustrate structure which can be implemented by the present invention to achieve, for example, scanning.

A very broad aspect of the present invention comprises supplying an atomized distribution of fluid particles in the path of a scanned beam to achieve electromagnetically induced mechanical cutting. In the illustrated embodiment of FIG. 1*a*, the output tip of the fiber optic is preferably maintained a few millimeters from the target. In the embodiment of FIG. 1*a*, the entire lower surface of the scanning housing is open. Other embodiments may comprise smaller openings which are only large enough to allow energy from the scanned fiber optic to exit the scanning housing. In modified embodiments, a transparent member may be provided over the lower surface of the scanning housing or the smaller opening to protect the internal components of the scanning housing.

Figure 2A:
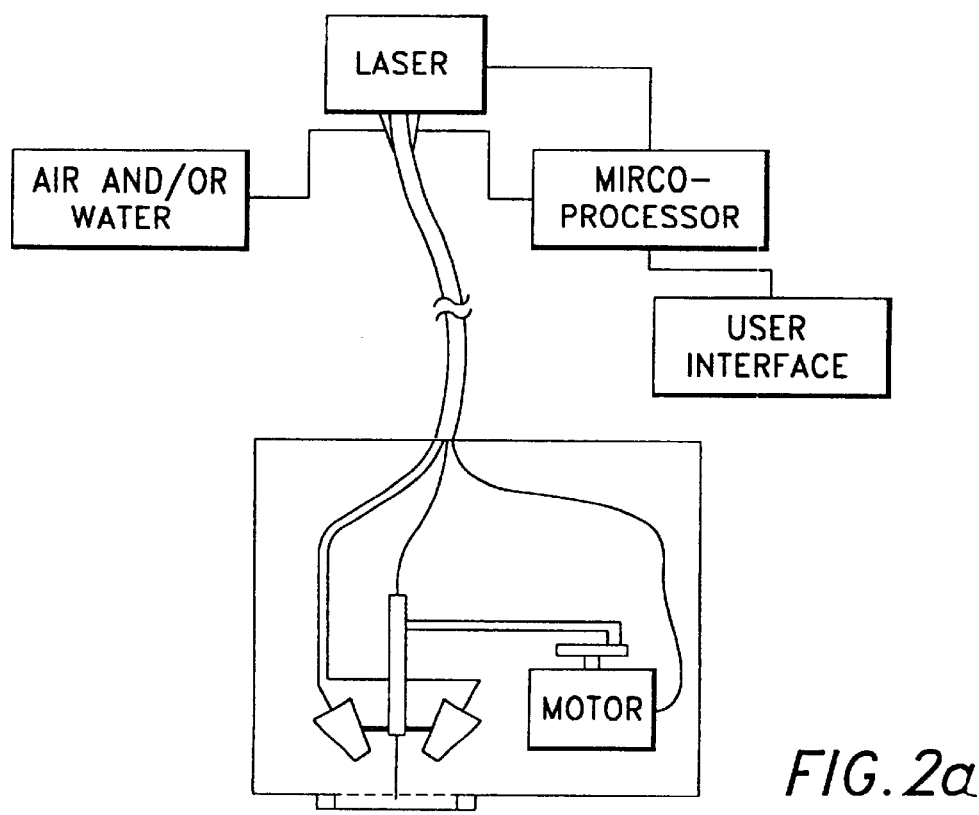

FIG. 2a illustrates an embodiment wherein the scanning housing comprises the motor. In the embodiment of FIG. 2a, a small opening exists, which as illustrated generally comprises a diameter equal to the distance between the two atomization nozzles. The size of this opening can be configured during design and manufacture thereof to accommodate the desired scanning patterns achievable by the motor and fiber optic combination. In FIG. 2a, a ring is attached at the bottom of the scanning housing. In the absence of the ring, in an event in one embodiment where the scanning housing is placed on the target surface, such as skin, although such placement is not required, the fiber optic tip is close to or touches the target surface. The ring of FIG. 2a can thus provide an exact spacing between the fiber optic tip (for outputting radiation) and the target surface, by contacting the target or a perimeter surface of the target.

Figure 1A:
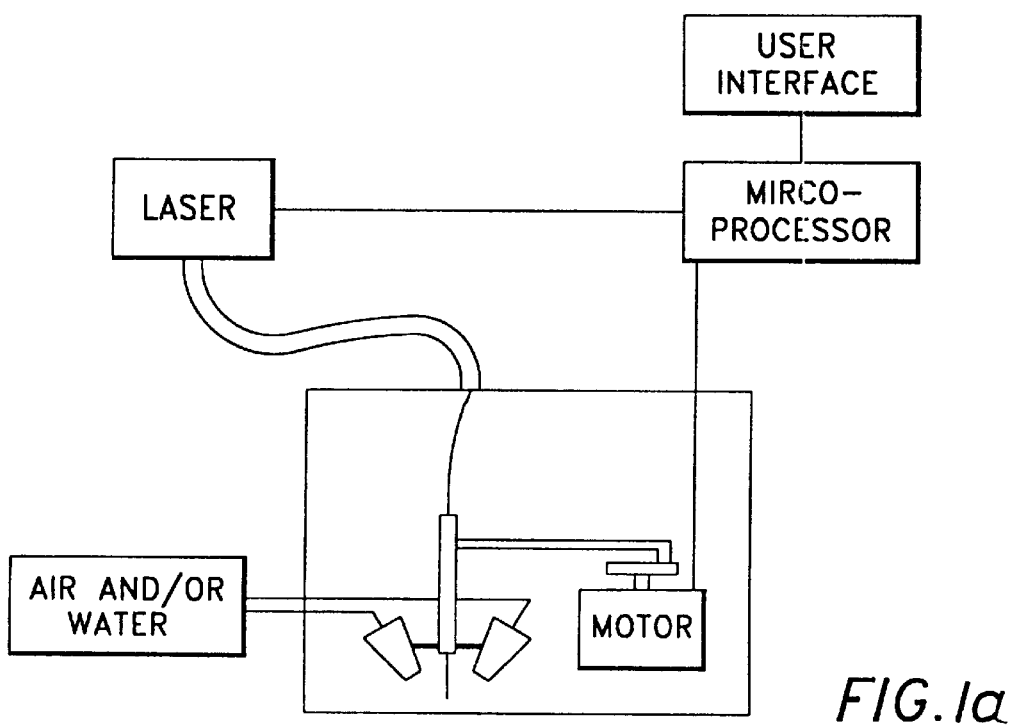

The ring can be configured to comprise a mist disk, as discussed in connection with FIGS. 3a–8b below. In the embodiments of FIGS. 1a and 2a, as well as the following embodiments, the microprocessor can be programmed to vary the velocities of the atomized fluid particles, the sizes of the atomized fluid particles, the distributions of the atomized particles, as well as other parameters of the atomized fluid particles, in accordance with desired cuts to be achieved. Additionally, these parameters of the atomized fluid particles may be varied in accordance with the surface being disrupted (for example, particular type or condition of skin or other type of soft tissue) by the electromagnetically induced mechanical cutter. In the embodiments of FIGS. 1*a* and 2*a,* as well as the additional embodiments illustrated in the following figures, a surface-profile imager/generator can be implemented to provide a computer generated model of a surface being scanned, as disclosed in U.S. Pat. No. 5,588,428. A visible beam, for example, may be used to collect profile information of the skin target surface. The electromagnetic energy from the fiber optic tip can be scanned accordingly in the embodiments of FIGS. 1*a* and 2*a,* and especially in the embodiments of FIGS. 3*a*–5*a* where a collimated beam is not necessarily used. Additionally, the amount and properties of the atomized fluid particles may be varied in accordance with different areas and/or desired disruptive forces desired to be imparted onto the modeled surface or different areas of the modeled surface.

In the embodiments of FIGS. 1*a* and 2*a,* the actual optical fiber is scanned using a motor assembly. Although the optical fiber may be scanned using a motor assembly in FIGS. 3*a* and 4*aa,* one embodiment of these figures can comprise the scanning of non-collimated electromagnetic energy using reflectors and focusing lenses, as known in the art. U.S. Pat. No. 5,624,434, and patents and references cited therein, disclose apparatuses which scan a non-collimated beam using dynamically controlled deflectors, the contents of which are expressly incorporated herein by reference. In other embodiments, similar technology may be incorporated in hand-held pieces, wherein a few or substantially all of the parts therein are fixed and do not move, and wherein the hand piece is moved instead. In FIG. 3*a,* a fiber optic feeds a scanning head with the laser energy from a laser, and subsequently, the laser energy exits the fiber optic and is deflected with motor-controlled mirrors or other means and is passed through focusing lenses. The focused beam then passes through a mist disk before impinging on the target surface. The mist disk is preferably configured to generate a thin layer of atomized fluid particles just over the target. The mist disk may be configured to have circular or other geometrical shapes. In the illustrated exemplary embodiment, the mist disk generates a layer of atomized fluid particles that is approximately 2 to 3 millimeters thick. Thinner and thicker layers are possible in substantially modified embodiments. The atomized fluid particles themselves are generally preferred to be on the order of microns in diameter. In a preferred embodiment, the atomized fluid particles have diameters within a range of about 40 to 60 microns. In other embodiments, the atomized fluid particles have diameters of approximately 200 microns. Other diameters are also possible in accordance with the present invention, so long as electromagnetically induced mechanical cutting is maximized and thermal effects, preferably, are attenuated or eliminated during implementation of non-thermal cutting operations. Since the electromagnetic energy from the laser is preferably highly absorbed by the atomized fluid particles, the layer of atomized fluid particles just above the target must be relatively thin in the presently preferred embodiment. In alternative embodiments, the layer of atomized fluid particles may be greater than 2 to 3 millimeters, but the amount of laser energy and/or characteristics of the distribution of atomized fluid particles must be adjusted accordingly so that cutting is maximized and thermal effects are attenuated or eliminated during implementation of non-thermal cutting operations. For example, for a substantially thicker layer of atomized fluid particles a substantially greater laser energy concentration must be introduced to penetrate the greater thickness of the layer of atomized fluid particles and to generate the proper mechanical-cutting effects on the surface. The dynamic deflecting and focusing system may comprise, for example, one or more motors controlling one or more deflecting lenses, and/or one or more focusing optics, for focusing the deflected electromagnetic energy above the target surface just above or within the mist disk. Each motor can comprise a galvanic motor or stepper motor, or example.

FIG. 4*aa* illustrates a schematic example where a motor controls a reflector assembly, and a focusing assembly is disposed between the reflector assembly and the mist disk. A shutter may be used, as shown in phantom in FIG. 4*aa,* for blocking the electromagnetic energy during intermediate positions between deflections, as is known in the art. In accordance with the present invention, a mist disk is placed between the target surface and the incident electromagnetic energy to provide the thin layer of atomized fluid particles. FIG. 5*a* illustrates a very thin mist disk, for providing an even thinner distribution of atomized fluid particles between the incident electromagnetic energy and the target. In FIG. 5*a,* a motor is used to scan a fiber optic. A phantom coupling is illustrated to the right of the motor, as an alternative to the coupling illustrated below and to the right of the motor, for scanning the fiber optic. Positioning of the coupling connector further away from the output tip of the fiber optic results in small movements of the coupling connector for scanning the output tip of the fiber optic. In the presently preferred embodiment, the fiber optic is flexible in a region between where the fiber optic enters the scanning housing and where the fiber optic is controlled by the motor. The fiber optic, however, is preferably rigid or stiff in a region between the coupling of the fiber optic by the motor and the output tip of the fiber optic.

FIGS. 6*a*–8*b* illustrate three exemplary embodiments of mist disks in accordance with the present invention. FIG. 6*a* is a side-elevation view of a mist disk, and FIG. 6*b* is a bottom planar view of a mist disk. Although mist disks are described and illustrated, any assembly for providing a thin layer of atomized fluid particles just above the target surface may be implemented, provided the laser energy can be concentrated into the layer of particles. For example, a single nozzle (without a mist disk) may be placed just adjacent to a fiber optic for providing an atomized distribution of fluid particles to the fiber optic or other means of introducing electromagnetic radiation, and the electromagnetic radiation may or may not be scanned. Additionally, one or more nozzles may be placed in conjunction with the fiber optic just above the target surface being scanned. The one or more nozzles may be scanned, themselves, as illustrated in FIGS. 9a–11a. In FIGS. 6a and 6b, two nozzles for outputting atomized fluid particles are placed within the disk at 180 degrees from each other. The two nozzles are supplied with air and/or water to generate a thin layer of atomized fluid particles. The thin layer of atomized fluid particles is preferably consistent over the scanning pattern of the electromagnetic energy impinging on the target surface. In addition to two nozzles, a greater number of nozzles may be implemented, as shown in phantom in FIG. 6b. The number of atomization nozzles may be adjusted according to design parameters. FIGS. 7a and 7b illustrate an embodiment where several fine nozzle outputs are placed along the height of the mist disk. In FIG. 7b, a relatively large number of output nozzles are also distributed along an inner circumference of the mist disk. The number of nozzles along the height and along the circumference of the mist disk can be adjusted in accordance with design parameters. The double-ended arrows shown in FIGS. 6a and 7a show that, in alternative embodiments, the nozzles within the disks may be moved along the axes of the arrows. In the presently preferred embodiment, the mist disks are removable from the scanning housing, and are all interchangeable, to thereby accommodate a large variety of different atomized distribution patterns which can be placed above the target surface. FIGS. 8a and 8b illustrate another embodiment where a misting substance, such as a fabric or a very thin screen, or other substance, is placed between the radially outwardly located air and/or water supply lines/sources and the scanning area of the electromagnetic energy. FIG. 8 illustrates a plurality of output nozzles being positioned radially outwardly of the material, but in alternative embodiments only a single output nozzle may be supplied along the height in the mist disk.

Figure 9A:
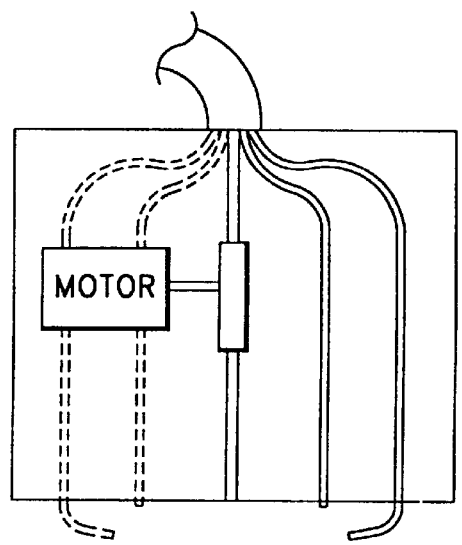

FIG. 9a illustrates a scanning housing where a motor scans a fiber optic, and where a single air supply is directed in a direction above the target surface basically parallel to the surface being scanned by the fiber optic. A fluid supply is positioned between the scanned fiber optic and the pressurized air supply, for directing fluid, such as water, into a pressurized exit path of the air supply. The resulting combination of the pressurized air line and the fluid line is to create an atomized distribution of fluid particles between the scanned fiber tip and the target surface.

The air and water lines may be placed closer to the fiber optic in alternative embodiments and may be configured in various orientations relative to one another, so long as fluid particles are generated in a distribution comprising a thin layer above the target surface. An additional air and water supply line is illustrated in phantom in FIG. 9a, and additional air and water lines may be added in accordance to design parameters.

Figure 10A:
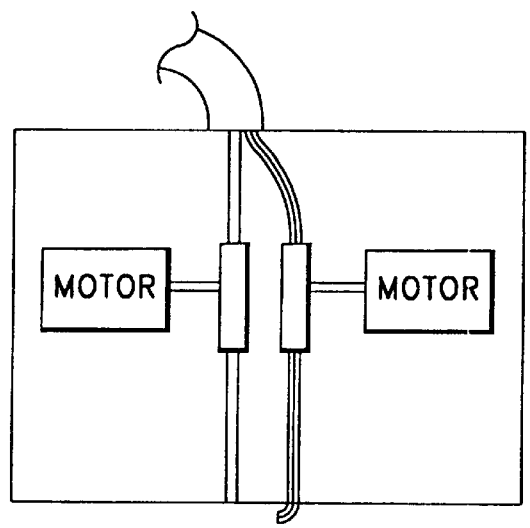
Figure 11A:
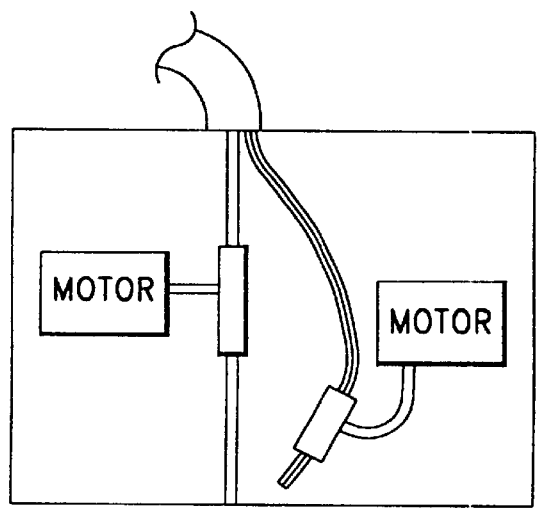

FIG. 10a illustrates an embodiment where a motor scans a fiber optic and where, additionally, a motor scans an air and/or water line. The two motors are preferably designed to work together to optimize a placement of atomized fluid particles at the output of the scanned fiber optic, to thereby achieve consistent results on the target surface. FIG. 11a illustrates an additional embodiment where a second motor is used to scan an air and/or water supply to dynamically place a consistent layer of atomized fluid particles in front of the output end of the movable fiber optic. The two motors may work together, based upon information obtained by a surface model of the target being scanned, for example, the surface model being predetermined or computer generated in accordance with known technology, such as disclosed in U.S. Pat. No. 5,588,428.

In addition to the scanning housings and/or mist disks illustrated in FIGS. 1a–11a, spacing arms or other spacing means may be connected to the scanning housings for providing a spacing between the scanning housings and the target surface. These spacing means may comprise one or more legs, for example. In one embodiment the spacing means can be about 3 millimeters. Other substantially different sizes may be used in other embodiments so long as a resulting disruptive mechanical forces, preferably without thermal effects in one configuration, are imparted onto the target surface. The size of the spacing means can range, for example, in accordance with the target, laser, and type and distribution of air and/or fluid particles selected. A collimated beam, for example, may facilitate greater dimensions in the spacing means. A single spacing arm connected to a scanning housing may be incorporated, for example. Such a spacing arm may be implemented in accordance with the present invention, so long as the spacing arm is short and, preferably, on the order of 2 to 3 millimeters. Additional technology disclosed in U.S. Pat. No. 5,611,795 is also incorporated herein by reference for disclosing various means of scanning electromagnetic energy over a target surface. In modified embodiments, single-nozzle fluid outputs oriented to output distributions of fluid particles preferably in directions substantially perpendicular to directions of incidence of the electromagnetic radiation, can be implemented. In addition, a piezoelectric atomizer for generating a fine spray may be used. Moreover, various configurations implementing fluid injectors, having structures similar to fuel injectors of internal combustion engines, for example, may be used to generate atomized distributions of fluid particles.

In modified embodiments, only a single line, as distinguished from separate water and separate air lines, is used to deliver moist air. The moist air may comprise a colloidal suspension of water droplets, very humid air (about 100% humid), cool or cold steam as from a cold humidifier, or water vapor from dry ice. A pulsing valve may be incorporated to control the delivery of fluid. In another embodiment, a mono-water droplet dispersor may be used to supply single droplets, or droplets of relatively small numbers, to the interaction zone.

Sprays can be used which are fed only by water without any assistance by an air line. A nebulizer, which uses air pressure and water to output atomized fluid particles through a small orifice, can be implemented. The nebulizer may comprise an ultrasonic or sonic device, and the atomized fluid particles may comprises water droplets having diameters ranging from about 5 to about 20 microns.

In accordance with the present invention, the fluid particles placed above the target surface may comprise materials other than, or in addition to, water. The fluid may comprise, for example, a medicated substance, a sterilized substance, or an anesthetic. U.S. Pat. No. 5,785,521 is expressly incorporated herein by reference to disclose, for example, various means and types of conditioned fluids which may be used in conjunction with a source of electromagnetic energy.

The present invention, which implements electromagnetically induced mechanical cutting to cut, remove, or otherwise impart disruptive mechanical forces onto relatively large surface areas of an epidermis, can be implemented on other target surfaces as well. The present invention is not intended to be limited to operating on skin, or even tissue. One preferred application, however, involves removing tissue from relatively large surface areas of the epidermis for cosmetic purposes. For example, cosmetic surgery may be implemented using the present device on the face of a patient. Other conventional means for scanning a collimated or non-collimated beam, which are not disclosed above, may be implemented for achieving this purpose. The apparatus of the present invention, however, differs from the prior art in implementing the atomized distribution of fluid particles between the impinging electromagnetic energy and the target surface. A particular laser source, as disclosed in U.S. application Ser. No. 08/903,187, filed Jun. 12, 1997 (now U.S. Pat. No. 6,288,499), is preferred, the contents of which are expressly incorporated herein by reference.

In a presently preferred embodiment of cosmetic surgery on the epidermis of a patient, the fluid particles or moist air may comprise at least one anesthesia and/or medication. Medications can include drugs for relieving pain (analgesics), such as Acetaminophen; drugs for causing a loss of general sensation (anesthetics), such as lidocaine or a combination of lidocaine & epinephrine; and substances able to kill or inhibit growth of certain microorganisms (antibiotics), such as penicillin or tetracycline.

When multiple passes of the electromagnetically induced mechanical cutter are conducted over the surface being ablated, the medication and/or anesthesia within the atomized fluid particles is continuously delivered onto the tissue, to thereby hydrate, relax, medicate, and/or otherwise treat or medicate the tissue. In alternative embodiments, the mist is applied only on the second of two passes over the surface. The mist may be applied at selected times during a single pass, and/or may be applied during selected passes of the laser over the surface. Similarly, the type of conditioning of the fluid may be selectively applied.

Prior art lasers typically do not apply any medication medium during the passing of laser over the skin, thereby causing the skin to become irritated and red.

In contrast to prior art lasers which typically impart thermal cutting forces onto the skin, the electromagnetically induced mechanical cutter of the present invention when operated in a non-thermal cutting mode preferably does not deliver any substantial amount of heat to the tissue. As mentioned above, the exploded atomized fluid particles are cooled by exothermic reactions before they contact the target surface. Thus, in accordance with one aspect of the present invention, atomized fluid particles of the present invention are heated, expanded, and cooled before contacting the target surface. Prior-art devices, which thermally operate on the skin, may have negative side effects associated therewith in connection with the medical procedure and the subsequent healing of the tissue. The present invention may, additionally, be able to ablate extremely thin layers of tissue, relative to existing laser skin surgery devices.

The substantially non-thermal cutting or reduced-thermal cutting alone, or in combination with the medicated atomized fluid particles, can serve to reduce erythema (skin redness) and reduce edema (swelling). Moreover, the present invention can serve to reduce unwanted thermal damage to adjacent tissue. For example, direct and/or adjacent melanocytes may not be substantially thermally damaged with the present invention, thus attenuating hypo or hyper pigmentation effects, which can occur with prior-art chemical peel, derma-abrasion (use of wire brush), and thermal-cutting laser procedures. The present invention further can serve to reduce post and intra-operative pain and discomfort. For example, burning sensations and effects experienced by the patient can be attenuated.

Relatively small surface areas, or small thicknesses, of the skin may be treated in low wattage modes, wherein a wattage is set from about one half to about 1 Watt. Additionally, a relatively small amount of fluid may be used. Alternatively, the electromagnetic energy may be applied in a defocused mode, for a net decrease in energy density on the target surface.

The above-mentioned delivery of the atomized fluid particles, which may comprise medication and/or anesthesia, onto the skin during or close in time with the cutting or ablating operation serves to hydrate, relax, medicate, and/or otherwise treat or medicate the tissue. The atomized fluid particles may be delivered into the interaction contemporaneously with each pulse of electromagnetic radiation or, alternatively, may be continuously delivered into the interaction zone.

Although the hydration of the soft tissue is a benefit in accordance with one aspect of the present invention, too much water can interfere with the optimal execution of the medical procedure. A percentage of the atomized fluid particles not within the path of the electromagnetic radiation will accumulate on the surface of the target surface. Suction can be used to remove excess or unwanted liquid from the target surface or adjacent areas. Cut tissue can be carried by the excess water and removed by the suction. In one embodiment, the target surface can be oriented so that gravity will drain off unwanted liquid. Suction can additionally, or alternatively, be used to remove airborne atomized fluid particles that are not in the interaction zone. One or more suction channels may be placed in a mist disk, for example, for removing unwanted, airborne atomized fluid particles not within the path of the electromagnetic energy. The suction channels may be placed between fluid output channels at the same height, or at different heights in which case the suction channels may also be placed directly above or below the fluid outputs channels. Utilization of the above-mentioned moist air, alone or in combination with atomized fluid particles, may help to attenuate an amount of excess fluid accumulating on the target surface.

Although an exemplary embodiment of the invention has been shown and described, many changes, modifications and substitutions may be made by one having ordinary skill in the art without necessarily departing from the spirit and scope of this invention.

What is claimed is:

1. An apparatus for imparting disruptive forces onto a target surface, comprising:

a scanner constructed to provide electromagnetic energy and to automatically scan the electromagnetic energy above a plurality of points of the target surface; and a moisture output constructed to simultaneously place a layer of moisture above the plurality of points, the placement of the layer of moisture above the plurality of points defining a corresponding plurality of interaction zones extending about 5 mm or less above the target surface, the electromagnetic energy from the scanner being automatically scanned over the layer of moisture and being substantially absorbed by the layer of moisture in each of the interaction zones, the substantial absorption of the electromagnetic energy in each of the interaction zones causing the moisture therein to expand and impart disruptive forces onto the target surface.

2. The apparatus as set forth in claim 1, wherein:

the electromagnetic energy from the scanner is substantially absorbed by the moisture above the plurality of points in a corresponding plurality of interaction zones;

each interaction zone is substantially bounded in a dimension, measured in a direction parallel to a direction of propagation of the electromagnetic radiation, that is no larger than about 5 mm from the target surface;

an amount of moisture extending beyond the 5 mm boundary of each interaction zone in a path of the electromagnetic radiation is negligible, so that an amount of absorption of the electromagnetic radiation by the moisture beyond each 5 mm boundary does not detectably alter the cutting power of the apparatus, compared to a cutting power that the apparatus would have if no moisture extended beyond the 5 mm boundary of each interaction zone.

3. The apparatus as set forth in claim 1, wherein:

the scanner comprises a fiber optic having an output end; and the moisture output is constructed to output moisture onto the output end of the fiber optic.

4. The apparatus as set forth in claim 1, wherein the electromagnetic energy comprises laser energy from one of an Er, Cr:YSGG solid state laser having a wavelength of about 2.78 microns and an Er:YAG solid state laser having a wavelength of about 2.94 microns.

5. The apparatus as set forth in claim 1, wherein the moisture comprises one of a colloidal suspension of water droplets, very humid air, cool or cold steam, and water vapor generated from a presence of dry ice.

6. The apparatus as set forth in claim 1, wherein the scanner operates in a first mode wherein the moisture output simultaneously places moisture above the plurality of points, and operates in second mode wherein the moisture output places no moisture above the plurality of points.

7. The apparatus as set forth in claim 1, wherein the scanner operates in a first mode wherein the moisture output simultaneously places moisture above the plurality of points, and operates in second mode wherein the moisture output places a reduced amount of moisture above the plurality of points, relative to an amount of moisture placed above the plurality of points by the moisture output in the first mode.

8. The apparatus as set forth in claim 1, wherein each interaction zone, in which the moisture is absorbing the electromagnetic energy and expanding, does not extend more than about 3 mm above the target surface.

9. The apparatus as set forth in claim 8, wherein the concentrated electromagnetic energy from the scanner has a wavelength which is highly absorbed by the moisture above the plurality of points.

10. The apparatus as set forth in claim 1, wherein the moisture output comprises at least one suction channel that removes at least a portion of atomized fluid particles output by the moisture output.

11. The apparatus as set forth in claim 10, wherein the suction channel removes airborne moisture.

12. The apparatus as set forth in claim 1, wherein the moisture comprises atomized fluid particles.

13. The apparatus as set forth in claim 12, wherein the moisture output comprises a nubulizer.

14. The apparatus as set forth in claim 12, wherein the moisture output comprises a piezoelectric element.

15. The apparatus as set forth in claim 1, wherein the scanner scans electromagnetic energy above a different one of each of the plurality of points at a different instance in time.

16. The apparatus as set forth in claim 15, wherein the scanner delivers a peak concentration of electromagnetic energy above each of the plurality of points, each peak concentration of electromagnetic energy being greater than a concentration of electromagnetic energy delivered onto the target surface.

17. The apparatus as set forth in claim 16, wherein the scanner delivers, regardless of whether moisture is placed above the plurality of points, a peak concentration of electromagnetic energy above each of the plurality of points that is greater than a concentration of electromagnetic energy delivered onto the target surface above each of the plurality of points.

18. The apparatus as set forth in claim 1, wherein:

the scanner is constructed to emit electromagnetic radiation along propagation paths extending distally away from the apparatus; and the moisture output is adapted to direct moisture in directions which are substantially perpendicular to the propagation paths.

19. The apparatus as set forth in claim 18, wherein:

the electromagnetic energy from the scanner is substantially absorbed by the moisture above the plurality of points in a corresponding plurality of interaction zones; and each interaction zone, in which the moisture is absorbing the electromagnetic energy and expanding, extends a distance of about 5 mm or less along each propagation path, each interaction zone being bounded at a proximal end thereof on a propagation path by an absence of moisture and being bounded at a distal end thereof on the propagation path by an absence of any substantial amount of electromagnetic radiation that would if present be capable of imparting thermal cuffing affects onto a human-tooth; and a wavelength of the electromagnetic energy is selected to be highly absorbed by the moisture in each interaction zone, whereby the absorption of the electromagnetic radiation by the moisture generates disruptive mechanical forces which are suitable for cuffing or ablating skin.

20. The apparatus as set forth in claim 19, wherein the disruptive mechanical forces, as distinguished from thermal cutting forces, generate cuffing forces suitable for cutting or ablating skin placed within one of the interaction zones.

21. The apparatus as set forth in claim 1, wherein:

the moisture output comprises at least one moisture line; and the scanner is adapted to move the at least one moisture line to facilitate placement of moisture from the moisture output above the plurality of points.

22. The apparatus as set forth in claim 21, wherein the moisture comprises one of a colloidal suspension of water droplets, very humid air, cool or cold steam, and water vapor generated from a presence of dry ice.

23. The apparatus as set forth in claim 21, wherein the moisture comprises atomized fluid particles.

24. The apparatus as set forth in claim 23, wherein the moisture output comprises a nubulizer.

25. The apparatus as set forth in claim 23, wherein the moisture output comprises a piezoelectric element.

26. The apparatus as set forth in claim 23, wherein the moisture output comprises at least one suction channel that removes at least a portion of atomized fluid particles output by the moisture output.

27. The apparatus as set forth in claim 1, wherein the scanner comprises a reflector assembly and focusing optics constructed to scan the electromagnetic energy above the plurality of points of the target surface.

28. The apparatus as set forth in claim 27, wherein the scanner is constructed to scan a collimated laser beam.

29. The apparatus as set forth in claim 27, wherein the moisture comprises one of a colloidal suspension of water droplets, very humid air, cool or cold steam, and water vapor generated from a presence of dry ice.

30. The apparatus as set forth in claim 27, wherein the moisture comprises atomized fluid particles.

31. The apparatus as set forth in claim 30, wherein the moisture output comprises a nubulizer.

32. The apparatus as set forth in claim 30, wherein the moisture output comprises a piezoelectric element.

33. The apparatus as set forth in claim 30, wherein the moisture output comprises at least one suction channel constructed to remove at least a portion of atomized fluid particles output by the moisture output.

34. The apparatus as set forth in claim 30, wherein the suction channel removes airborne moisture.

* * * * *